(12) United States Patent
Wu et al.

(10) Patent No.: US 11,990,624 B2
(45) Date of Patent: May 21, 2024

(54) POSITIVE ELECTRODE SLURRY, POSITIVE ELECTRODE PLATE, AND SECONDARY BATTERY INCLUDING SUCH POSITIVE ELECTRODE PLATE

(71) Applicant: CONTEMPORARY AMPEREX TECHNOLOGY CO., LIMITED, Ningde (CN)

(72) Inventors: Qifan Wu, Ningde (CN); Ming Zhang, Ningde (CN)

(73) Assignee: CONTEMPORARY AMPEREX TECHNOLOGY CO., LIMITED, Ningde (CN)

( * ) Notice: Subject to any disclaimer, the term of this patent is extended or adjusted under 35 U.S.C. 154(b) by 0 days.

(21) Appl. No.: 18/340,019

(22) Filed: Jun. 22, 2023

(65) Prior Publication Data
US 2023/0369595 A1  Nov. 16, 2023

Related U.S. Application Data

(63) Continuation of application No. PCT/CN2022/091917, filed on May 10, 2022.

(51) Int. Cl.
*H01M 4/62* (2006.01)
*C07C 43/23* (2006.01)
(Continued)

(52) U.S. Cl.
CPC .............. *H01M 4/62* (2013.01); *C07C 43/23* (2013.01); *H01M 4/131* (2013.01); *H01M 4/136* (2013.01);
(Continued)

(58) Field of Classification Search
None
See application file for complete search history.

(56) References Cited

FOREIGN PATENT DOCUMENTS

| CN | 109585922 A | 4/2019 |
| CN | 111224076 | * 6/2020 |

(Continued)

OTHER PUBLICATIONS

The World Intellectual Property Organization (WIPO) International Search Report and Written Opinion for PCT/CN2022/091917 Jan. 16, 2023 13 pages (including English translation).

*Primary Examiner* — Laura Weiner
(74) *Attorney, Agent, or Firm* — ANOVA LAW GROUP, PLLC

(57) ABSTRACT

A positive electrode slurry contains polyether polyol, where the polyether polyol has the following constitutional formula:

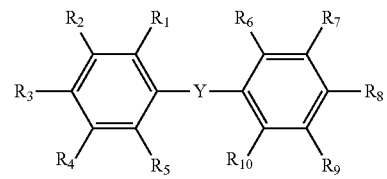

where $R_1$, $R_2$, $R_3$, $R_4$, $R_5$, $R_6$, $R_7$, $R_8$, $R_9$, $R_{10}$, and Y are as defined in the specification.

12 Claims, 2 Drawing Sheets

(51) Int. Cl.
*H01M 4/131* (2010.01)
*H01M 4/136* (2010.01)
*H01M 4/525* (2010.01)
*H01M 4/58* (2010.01)
*H01M 4/02* (2006.01)

(52) U.S. Cl.
CPC ............. *H01M 4/525* (2013.01); *H01M 4/58* (2013.01); *H01M 4/5825* (2013.01); *H01M 2004/021* (2013.01); *H01M 2004/028* (2013.01)

(56) References Cited

FOREIGN PATENT DOCUMENTS

| | | | |
|---|---|---|---|
| JP | 9-274933 | * | 10/1997 |
| JP | 2014191942 A | | 10/2014 |

* cited by examiner

POSITIVE ELECTRODE SLURRY, POSITIVE ELECTRODE PLATE, AND SECONDARY BATTERY INCLUDING SUCH POSITIVE ELECTRODE PLATE

CROSS-REFERENCE TO RELATED APPLICATION

This application is a continuation of International Application No. PCT/CN2022/091917, filed on May 10, 2022, the entire content of which is incorporated herein by reference.

TECHNICAL FIELD

This application relates to the field of lithium battery technologies, and in particular, to a positive electrode slurry and positive electrode plate containing polyether polyol; and furthermore, this application further relates to a secondary battery and battery module including such positive electrode plate.

BACKGROUND

In recent years, with increasingly wide use of lithium-ion batteries, lithium-ion batteries have been widely used in energy storage power supply systems such as hydroelectric, thermal, wind, and solar power plants, and many other fields including electric tools, electric bicycles, electric motorcycles, electric vehicles, military equipment, and aerospace. Along with the great development of lithium-ion batteries, higher requirements are imposed on the improvement of their energy density and the reduction of their costs.

Currently, one of effective ways to improve the energy density of lithium-ion batteries is to increase the coating mass of positive electrode plates. However, increasing the coating mass of positive electrode plates leads to serious risks in the manufacture of electrode plates. Increasing the coating mass of positive electrode plates can also lead to difficulties in cell fabrication because the characteristics of positive electrode slurries and the characteristics of electrode plates directly affect cell fabrication.

Therefore, the positive electrode plates still need to be improved.

SUMMARY

This application is made in view of the preceding subject matter and aims to provide a positive electrode slurry containing specific polyether polyol, a positive electrode plate prepared using such positive electrode slurry, and a secondary battery and battery module including such positive electrode plate.

Accordingly, a first aspect of this application provides a positive electrode slurry including a positive electrode active material and polyether polyol. The polyether polyol has the following constitutional formula:

formula 1 where
$R_1$, $R_2$, $R_3$, $R_4$, $R_5$, $R_6$, $R_7$, $R_8$, $R_9$, and $R_{10}$ are each independently selected from H, a hydroxyl group, halogen, —$CH_3$, and X;
where
X has the following constitutional formula:

formula 2 where
n is an integer ranging from 6 to 1000, optionally ranging from 14 to 1000, and most optionally ranging from 20 to 500; and
D is H or a $C_{1-8}$ alkyl group;
each R is independently selected from H, halogen, a hydroxyl group, a halogenated $C_{1-8}$ alkyl group, $R_{11}$, —$OR_{11}$ or $R_{11}OR_{12}$, where $R_{11}$ and $R_{12}$ are each independently selected from a straight-chain or branched-chain $C_{1-8}$ alkyl group, a phenyl group, a $C_{1-8}$ alkyl substituted phenyl group, a $C_{1-8}$ alkoxy substituted phenyl group, or a halogenated phenyl group; and optionally, each R is independently H, $R_{11}$, or a phenyl group;
at least one of $R_1$, $R_2$, $R_3$, $R_4$, $R_5$, $R_6$, $R_7$, $R_8$, $R_9$, and $R_{10}$ is X, wherein not both $R_1$ and $R_6$ are X, and not both $R_5$ and $R_{10}$ are X; and
Y is selected from a group having the following constitutional formula:
—O—, —S—, —$CH_2$—, —$CH(CH_3)_2$—, —$CH(CH_3)(CH_2CH_3)$—, —$CH(CH_3)(Ph)$-, —$CH(Ph)_2$-, —$CH(COOCH_3)$—, —$CH(COOCH_2CH_2CH_3)$—, and —$S(O)_2$—.

In any embodiment of this application, the energy density of a resulting lithium-ion battery is significantly increased after the polyether polyol is added to the positive electrode slurry. In addition, due to the improvement of the positive electrode plate, an amount of material for fabricating a cell can be saved, thus reducing the total material cost of the cell.

In any embodiment, the polyether polyol has a weight-average molecular weight ranging from 1000 to 50,000, optionally ranging from 2000 to 40,000, and more optionally ranging from 4000 to 40,000.

When the molecular weight is too small, the positive electrode slurry has poor stability, physical gelation is likely to occur, and a sheet resistance of the positive electrode deteriorates, which adversely affects the performance of the battery. When the molecular weight is too large, dispersion of the polyether polyol in the positive electrode slurry is not desirable. Therefore, the weight-average molecular weight of the polyether polyol should be controlled within the foregoing range.

Sufficient hydrogen bonds and a suitable amount of covalent bonds are formed among the polyether polyol, the positive electrode active material, and a collector, ensuring stability during preparation of the positive electrode plate, flexibility of the positive electrode plate, and dispersion of various positive electrode materials, thereby improving energy density of the battery.

In any embodiment, a mass ratio of the polyether polyol to the positive electrode active material ranges from 0.0005 to 0.040, optionally ranges from 0.001 to 0.02, more optionally ranges from 0.001 to 0.01, and most optionally ranges from 0.001 to 0.007.

When the ratio is too small, cracking of the positive electrode plate occurs at a high coating mass, and when the ratio is too large, the performance of the battery is adversely affected.

In any embodiment, the positive electrode active material is selected from at least one of lithium iron phosphate, lithium manganese iron phosphate, lithium manganese oxide, lithium cobalt oxide, lithium nickel cobalt manganese oxide, lithium nickel cobalt aluminate, lithium nickel oxide, or a mixture thereof.

When the positive electrode active material is at least one of lithium iron phosphate, lithium manganese iron phosphate, lithium manganese oxide, lithium cobalt oxide, lithium nickel cobalt manganese oxide, lithium nickel cobalt aluminate, lithium nickel oxide, or a mixture thereof, the addition of the polyether polyol can better achieve the effects of, for example, improving the flexibility of the electrode plate and increasing the maximum coating mass of the electrode plate.

In any embodiment, a gel state factor G of the positive electrode slurry ranges from 0 to 1, and optionally ranges from 0 to 0.3;

where $G=(m1-m2)/m1$, the slurry is determined not to be gelled when G ranges from 0 to 0.3, and the slurry is determined to be gelled when G is greater than 0.3;

m1 is a mass of a positive electrode slurry obtained after 2 kg of an initial positive electrode slurry is filtered for 10 minutes using a 100-mesh filter; and m2 is a mass of a positive electrode slurry obtained after 2 kg of a positive electrode slurry that has been left standing for 48 hours is filtered for 10 minutes using a 100-mesh filter; where the positive electrode slurry used for determining m1 and the positive electrode slurry used for determining m2 are from the same batch of positive electrode slurry.

The positive electrode slurry obtained by filtration after the positive electrode slurry has been left standing for 48 h has a mass more similar to the initially obtained mass of the positive electrode slurry and has a smaller G-value, indicating that the slurry is less prone to be gelled and the slurry has a better state. The anti-gelation performance of the positive electrode slurry described in this application is excellent.

A second aspect of this application provides a positive electrode plate including:
 a positive electrode current collector; and
 a positive electrode film layer on at least one surface of the positive electrode current collector, where the positive electrode film layer includes the positive electrode slurry according to the first aspect of this application. As mentioned above, with the polyether polyol added, this application allows the maximum coating mass of the positive electrode plate to be increased, which is also manifested in an increase in the maximum mass of the positive electrode film layer.

In any embodiment, the positive electrode film layer has a mass per unit area on the electrode plate ranging from 13 $mg/cm^2$ to 35 $mg/cm^2$, optionally ranging from 22 $mg/cm^2$ to 31 $mg/cm^2$, and more optionally ranging from 25 $mg/cm^2$ to 29 $mg/cm^2$, and the mass is a mass of a positive electrode film layer on a single surface of the electrode plate. If the positive electrode film layer is provided on each of two surfaces of the positive electrode plate, the positive electrode film layer has a mass per unit area on the electrode plate that is twice the foregoing range, to be specific, ranging from 26 $mg/cm^2$ to 70 $mg/cm^2$, optionally ranging from 44 $mg/cm^2$ to 62 $mg/cm^2$, and more optionally ranging from 50 $mg/cm^2$ to 58 $mg/cm^2$, and the mass is a mass of a positive electrode film layer on the two surfaces of the electrode plate.

When the mass per unit area of the positive electrode film layer on the electrode plate is too small, the electrode plate has undesirable uniformity; and when the mass per unit area of the positive electrode film layer on the electrode plate is too large, severe cracking occurs in the electrode plate coating process and the fabrication has to be interrupted. In this application, the mass per unit area of the positive electrode film layer on the electrode plate is limited within the foregoing range so as to ensure that the best effect can be achieved within this range.

The positive electrode plate described in this application has good flexibility and a significantly increased coating mass. Application of such positive electrode plate to a secondary battery, for example, adding the positive electrode slurry directly during preparation, can significantly improve the energy density of the battery.

In any embodiment, under the condition that flexibility of the positive electrode plate is measured using a winding needle in this application, when a diameter R of the winding needle is less than or equal to 3.0 mm, the positive electrode plate has no cracks produced; or when a diameter R of the winding needle is equal to 3.0 mm, the positive electrode plate has cracks produced, but when the diameter R of the winding needle is equal to 4.0 mm, the positive electrode plate has no cracks produced.

The addition of the polyether polyol described in this application reduces the cold pressing pressure, thereby reducing cracks and the risk of strip breakage, which in turn improves the flexibility of the electrode plate.

In any embodiment, the positive electrode plate has an infiltration increase rate I ranging from 2% to 20%, optionally ranging from 6% to 15%;

where $I=(I2-I1)/I1\times100\%$;

I2 is an infiltration rate of the positive electrode plate in an electrolyte; and I1 is an infiltration rate of a positive electrode plate containing no polyether polyol in an electrolyte;

where the positive electrode plate used for determining I1 is the same as the positive electrode plate used for determining I2, differing only in that the positive electrode plate used for determining I1 contains no polyether polyol, and the positive electrode plate used for determining I2 contains the polyether polyol.

The electrode plate with high infiltrability can realize good infiltration in the electrolyte and electrolyte retention, thus realizing effective infiltration into the electrode plate of the cell, avoiding inadequate infiltration into the electrode plate, improving the efficiency of electrolyte injection of the cell and the infiltration into the electrode plate during the cycling, and thus effectively improving the performance of battery products. The positive electrode plate described in this application has quite high infiltrability in the electrolyte.

A third aspect of this application provides a secondary battery including the positive electrode plate according to the second aspect of this application or a positive electrode plate obtained from the positive electrode slurry according to the first aspect of this application.

A fourth aspect of this application provides a battery module including the secondary battery according to the second aspect of this application.

A fifth aspect of this application provides a battery pack including the battery module according to the third aspect of this application.

A sixth aspect of this application provides an electric apparatus including at least one of the secondary battery according to the third aspect of this application, the battery module according to the fourth aspect of this application, or the battery pack according to the fifth aspect of this application.

DESCRIPTION OF EMBODIMENTS

The following specifically discloses embodiments of a positive electrode slurry and a manufacturing method thereof, a positive electrode plate, a secondary battery, a battery module, a battery pack, and an electrical apparatus in this application with appropriate reference to detailed descriptions of accompanying drawings. However, there may be cases where unnecessary detailed descriptions are omitted. For example, detailed descriptions of a well-known matter and repeated descriptions of actually identical structures have been omitted. This is to avoid unnecessarily prolonging the following description, for ease of understanding by persons skilled in the art. In addition, the accompanying drawings and the following descriptions are provided for persons skilled in the art to fully understand this application and are not intended to limit the subject matter recorded in the claims.

"Ranges" disclosed in this application are defined in the form of lower and upper limits. A given range is defined by one lower limit and one upper limit selected, where the selected lower and upper limits define boundaries of that particular range. Ranges defined in this method may or may not include end values, and any combinations may be used, meaning any lower limit may be combined with any upper limit to form a range. For example, if ranges of 60-120 and 80-110 are provided for a specific parameter, it is understood that ranges of 60-110 and 80-120 can also be envisioned. In addition, if minimum values of a range are given as 1 and 2, and maximum values of the range are given as 3, 4, and 5, the following ranges can all be envisioned: 1-3, 1-4, 1-5, 2-3, 2-4, and 2-6. In this application, unless otherwise stated, a value range of "a-b" is a short representation of any combination of real numbers between a and b, where both a and b are real numbers. For example, a value range of "0-5" means that all real numbers in the range of "0-5" are listed herein, and "0-5" is just a short representation of a combination of these values. In addition, a parameter expressed as an integer greater than or equal to 2 is equivalent to disclosure that the parameter is, for example, an integer among 2, 3, 4, 5, 6, 7, 8, 9, 10, 11, 12, and so on.

Unless otherwise specified, all the embodiments and optional embodiments of this application can be combined with each other to form new technical solutions.

Unless otherwise specified, all the technical features and optional technical features of this application can be combined with each other to form new technical solutions.

Unless otherwise specified, all the steps in this application can be performed in the order described or in random order, and optionally, in the order described. For example, a method including steps (a) and (b) indicates that the method may include steps (a) and (b) performed in order or may include steps (b) and (a) performed in order. For example, the foregoing method may further include step (c), which indicates that step (c) may be added to the method in any ordinal position, for example, the method may include steps (a), (b), and (c), steps (a), (c), and (b), steps (c), (a), and (b), or the like.

Unless otherwise specified, "include" and "contain" mentioned in this application are inclusive. For example, the terms "include" and "contain" can mean that other unlisted components may or may not also be included or contained.

Unless otherwise specified, in this application, the term "or" is inclusive. For example, the phrase "A or B" means "A, B, or both A and B". More specifically, any one of the following conditions satisfies the condition "A or B": A is true (or present) and B is false (or not present); A is false (or not present) and B is true (or present); or both A and B are true (or present). In this disclosure, the phrases "at least one of A, B, and C" and "at least one of A, B, or C" both mean only A, only B, only C, or any combination of A, B, and C.

Figure 2:
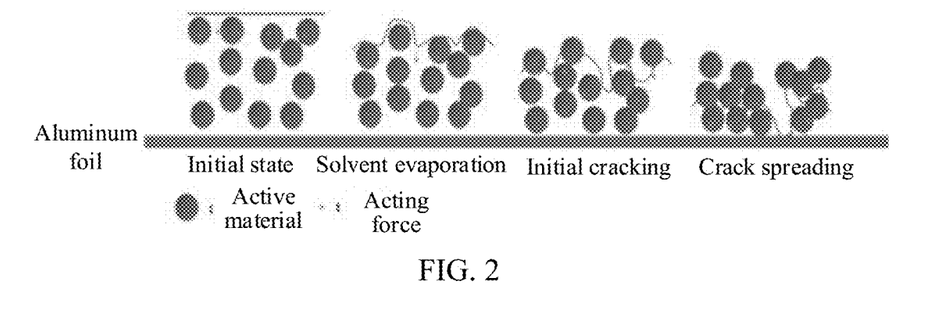
FIG. 2 is a schematic diagram of a process of coating cracking caused by capillary tension in a coating process of a positive electrode plate in the related art. In the figure, the active material is a positive electrode active material, the acting force is an acting force generated in the coating process, and the arrows represent directions of acting forces. In the coating process, the polyether polyol as described in this application is not used.

For lithium-ion batteries, increasing energy density is the trend. One way to improve energy density is to increase the coating mass of positive electrode plates. However, the inventors of this application have found that, as shown in FIG. 2, in the conventional coating process of positive electrode slurry, during or after solvent evaporation, a positive electrode plate cracks due to capillary tension, and the cracking spreads further, resulting in cracking in a large area. In addition, this process is accompanied by curling of the edge of the electrode plate. In addition, because the positive electrode plate is hard and brittle, it suffers from strip breakage in a cold pressing process and severe fracture at the inner ring in a winding process. In view of this, the inventors of this application have designed and synthesized a flexible polymer material: polyether polyol. The addition of this flexible material increases the coating mass, improves the coating quality, eliminates the risks caused in the cold pressing and winding processes, and reduces the total cost of materials used to fabricate a battery.

Accordingly, a first aspect of this application provides a positive electrode slurry including a positive electrode active material and polyether polyol. The polyether polyol has the following constitutional formula:

formula 1 where
R$_1$, R$_2$, R$_3$, R$_4$, R$_5$, R$_6$, R$_7$, R$_8$, R$_9$, and R$_{10}$ are each independently selected from H, a hydroxyl group, halogen, —CH$_3$, and X;
where
X has the following constitutional formula:

—O(CH$_2$—CHR—O)$_n$D     formula 2 where
n is an integer ranging from 6 to 1000, optionally ranging from 14 to 1000, and most optionally ranging from 20 to 500; and
D is H or a C$_{1-8}$ alkyl group;
each R is independently selected from H, halogen, a hydroxyl group, a halogenated C$_{1-8}$ alkyl group, R$_{11}$, —OR$_{11}$ or R$_{11}$OR$_{12}$, where R$_{11}$ and R$_{12}$ are each independently selected from a straight-chain or branched-chain C$_{1-8}$ alkyl group, a phenyl group, a C$_{1-8}$ alkyl substituted phenyl group, a C$_{1-8}$ alkoxy substituted phenyl group, or a halogenated phenyl group; and optionally, each R is independently H, R$_{11}$, or a phenyl group;
at least one of R$_1$, R$_2$, R$_3$, R$_4$, R$_5$, R$_6$, R$_7$, R$_8$, R$_9$, and R$_{10}$ is X, wherein not both R$_1$ and R$_6$ are X, and not both R$_5$ and R$_{10}$ are X; and
Y is selected from a group having the following constitutional formula:
—O—, —S—, —CH$_2$—, —CH(CH$_3$)$_2$—, —CH(CH$_3$)(CH$_2$CH$_3$)—, —CH(CH$_3$)(Ph)-, —CH(Ph)$_2$-, —CH(COOCH$_3$)—, —CH(COOCH$_2$CH$_2$CH$_2$CH$_3$)—, and —S(O)$_2$—.

In this application, halogen denotes fluorine, chlorine, bromine, or iodine, and optionally fluorine.

In this application, the C$_{1-8}$ alkyl group is a straight-chain or branched-chain alkyl group containing 1-8 carbons, and the straight-chain or branched-chain alkyl group containing 1-8 carbons may be selected from, for example, methyl, ethyl, propyl, butyl, pentyl, hexyl, heptyl, octyl, isopropyl, isobutyl, tert-butyl, isopentyl, tert-pentyl, neopentyl, 2-methylpentyl, 3-methylpentyl, 2,2-dimethylbutyl, 2,3-dimethyl butyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, 2-methylheptyl, 3-methylheptyl, 4-methylheptyl, 2,2-dimethylhexane, 3,3-dimethylhexane, 2,3-dimethylhexane, 2,4-dimethylhexane, 2,5-dimethylhexane, 3,4-dimethylhexane, 3-ethylhexane, 2,2,3-trimethylpentane, 2,2,4-trimethylpentane, 2,3,3-trimethylpentane, 2,3,4-trimethylpentane, 2-methyl-3-ethyl-pentane, 3-methyl-3-ethyl-pentane, and 2,2,3,3-tetramethylbutane.

In this application, the C$_{1-8}$ alkoxy group is a straight-chain or branched-chain alkoxy containing 1-8 carbon atoms, which includes, for example, ethoxy, propoxy, butoxy, tert-butoxy, pentyloxy, hexyloxy, heptoxy, octoxy, and their tautomers.

In this application, the halogenated C$_{1-8}$ alkyl group is a C$_{1-8}$ alkyl group substituted with one or more same or different halogens.

In this application, the C$_{1-8}$ alkyl substituted phenyl group is a phenyl group substituted with one or more same or different C$_{1-8}$ alkyl groups. The C$_{1-8}$ alkoxy substituted phenyl group is a phenyl group substituted with one or more same or different C$_{1-8}$ alkoxy groups.

In this application, the halogenated phenyl group represents a phenyl group substituted with one or more same or different halogens. In some embodiments, the halogenated phenyl group may be selected from, for example, 4-fluorophenyl, 2-fluorophenyl, 2,6-difluorophenyl, 4-(trifluoromethyl)phenyl, 4-chlorophenyl, 3-chlorophenyl, 4-bromophenyl, 3-bromophenyl, or 2-bromophenyl.

In this application, "Ph" is an abbreviation for phenyl.

Figure 1:
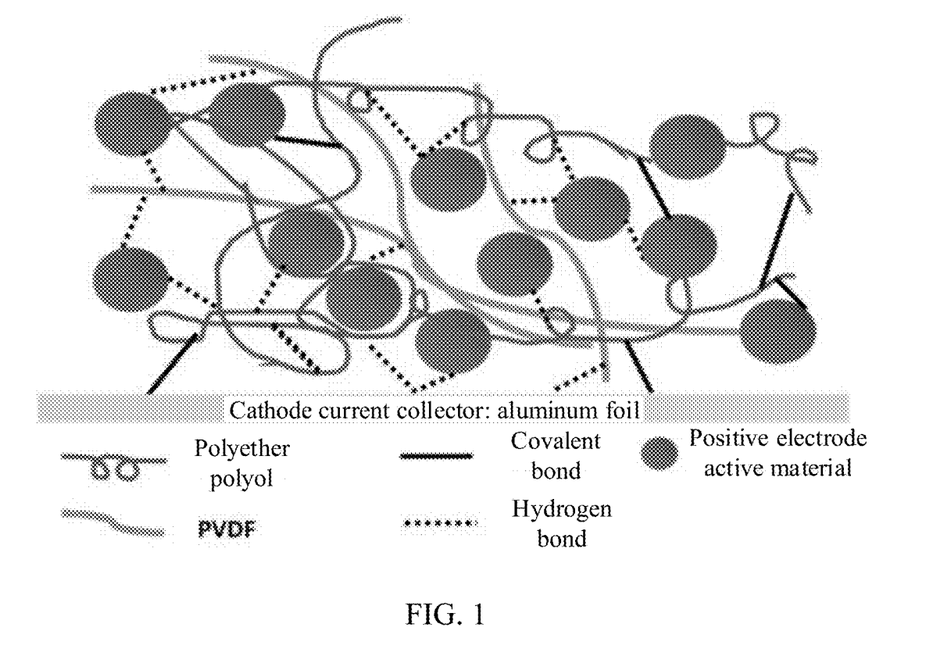
FIG. 1 is a schematic principle diagram of interaction between polyether polyol in a positive electrode plate of this application and other materials in the positive electrode plate, where the polyether polyol is the polyether polyol described in this application, a cathode current collector is a positive electrode current collector aluminum foil, and PVDF is a binder.
Figure 3:
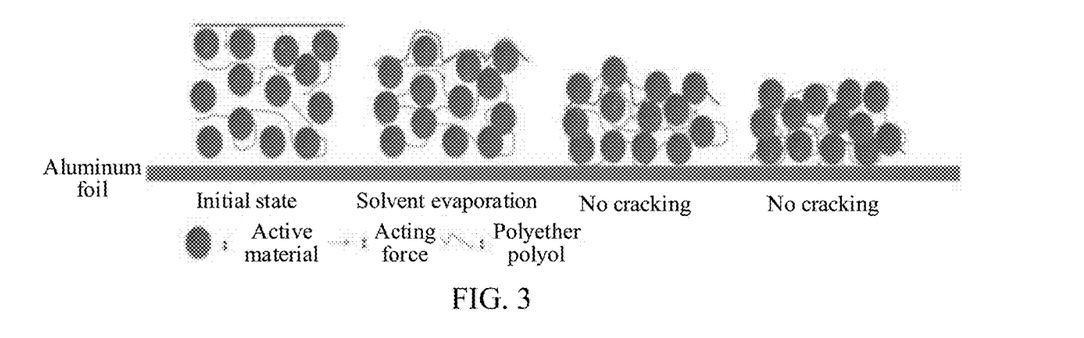
FIG. 3 is a schematic diagram of a positive electrode plate according to this application without cracking in a coating process. In the figure, the active material is a positive electrode active material, the acting force is an acting force generated in the coating process, and the arrows represent directions of acting forces. In the coating process, the polyether polyol as described in this application is used.
Figure 4:
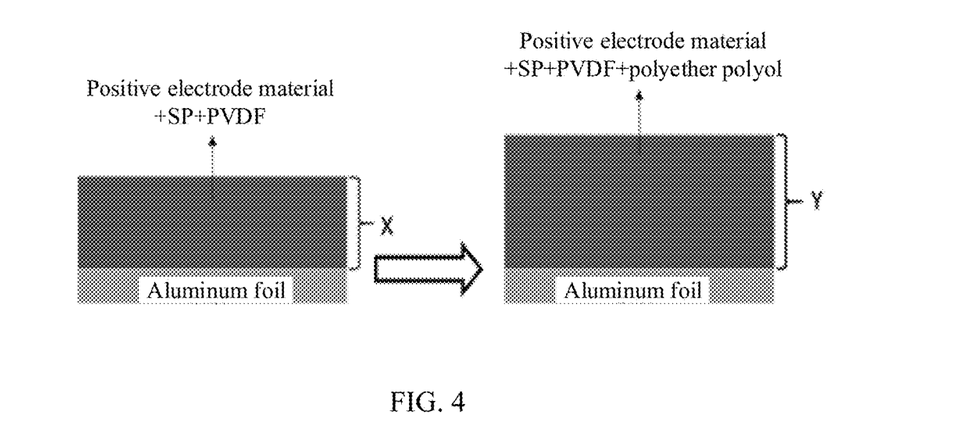
FIG. 4 is a schematic diagram showing an increase in a maximum coating mass per unit area of a positive electrode plate using polyether polyol in this application. In the figure, the positive material represents a positive electrode active material, SP represents a conductive agent used in the positive electrode plate, PVDF represents a binder used in the positive electrode plate, X represents a maximum coating thickness of the positive electrode slurry containing no polyether polyol, and Y represents a maximum coating thickness of the positive electrode slurry containing polyether polyol under the same condition. Apparently, Y is greater than X.

The polyether polyol described in this application contains flexible chain segments, which can disperse in the positive electrode slurry and also ensure the flexibility of the electrode plate. Hydrogen bonds or covalent bonds are formed between the polymers and between the polymer and surfaces of the positive electrode particles, ensuring that the positive electrode particles do not migrate in the coating process, as shown in FIG. 1. The polyether polyol has good compatibility with the electrolyte solvent, and does not affect the infiltration of the electrolyte into the surface of the positive electrode particles, ensuring its compatibility; and in the cold pressing process, the flexible chains stretch, which is manifested by decreasing the cold pressing pressure and reducing cracks and the risk of strip breakage. The polyether polyol of this application is of long flexible chains. Therefore, the addition of a flexible additive, that is, the polyether polyol described in this application, to the positive electrode slurry can improve the stability of the positive electrode slurry, improve the flexibility of the positive electrode plate, and ensure the dispersion of materials in the positive electrode plate, thereby increasing the coating mass of the positive electrode plate. As shown in FIG. 3, with the polyether polyol added, the positive electrode slurry of this application does not crack in the whole coating process. As shown in FIG. 4, the maximum coating thickness (mass) of the positive electrode plate is significantly increased after the polyether polyol of this application is added.

Optionally, the polyether polyol described in this application is added as it is (without further reaction) to the positive electrode slurry.

The polyether polyol described in this application may be obtained according to conventional technical means in the art or may be prepared in the following steps:
adding a catalyst, a regulator, an initiator, and an epoxy compound to an autoclave for reacting at 20° C. to 200° C. at a pressure of −0.1 MPa to 0.5 MPa for 1 h to 50 h to obtain crude polyether polyol, which is then neutralized, degassed, adsorbed, and vacuum filtered to obtain finished polyether polyol. The catalyst may be one of KOH or NaOH, the regulator may be one of ethylene glycol or propanetriol, an acid used for neutralization is one of sulfuric acid, phosphoric acid, and oxalic acid, and the initiator is one or more of bisphenol A, bisphenol S, bisphenol B, 2,4'-dihydroxydiphenylmethane, 4,4'-ethylenebisphenol, 4,4'-methylene bis(2-methylphenol), 4,4'-(1-phenylethyl)bisphenol, 4,4'-dibenzylidene bisphenol, 4,4-(2-methylpropylene) benzenediol, 4,4'-dihydroxydiphenyl sulfide, p-hydroxydiphenyl ether, methyl 2,2-bis(4-hydroxyphenyl)acetate, butyl 2,2-bis(4-hydroxyphenyl)acetate, and 4,4'-sulfonyldiphenol. In some embodiments, the epoxy compound is one or more of ethylene oxide, propylene oxide, epichlorohydrin, cyclohexane oxide, cyclobutoxane, tetrahydrofuran, 4-vinyl cyclohexane oxide, allyl glycidyl ether, styrene oxide, 1,2-epoxypentane, 1,2-epoxyheptane, 1,2-epoxyoctane, 1,2-epoxydecane, 1,2-epoxy-3-methylbutane, cyclo oxyfluoropropane, epichlorohydrin, epibromohydrin alkyl substituted styrene oxide, bisphenol A epoxy resin, phenol type phenolic resin, bisphenol S epoxy resin, 1,4-butanediol dishrink glyceryl ether, polypropylene glycol diglycidyl ether, polyethylene glycol diglycidyl ether, glycerol triglycidyl ether, trimethylolpropane triglycidyl ether, pentaerythritol tetraglycidyl ether, or epoxidized animal and vegetable oils.

The weight-average molecular weight of the polyether polyol can be controlled by the reaction time, the amount of catalyst, the amount of regulator, the amount of initiator, and the like.

In any embodiment of this application, the energy density of a resulting lithium-ion battery is significantly increased after the polyether polyol is added to the positive electrode slurry. In addition, due to the improvement of the positive electrode plate, an amount of material for fabricating a cell can be saved, thus reducing the total material cost of the cell.

In some embodiments, the polyether polyol has a weight-average molecular weight ranging from 1000 to 50,000, optionally ranging from 2000 to 40,000, and more optionally ranging from 4000 to 40,000.

The molecular weight has an effect on the processability of the positive electrode plate. In a case of small molecular weight, the flexibility of the positive electrode plate is not significantly improved, there will still be cracking in the coating, and there may be problems of strip breakage in cold pressing and fracture in winding. When the molecular weight is too small, the positive electrode slurry has poor stability, physical gelation is likely to occur, and a sheet resistance of the positive electrode deteriorates, which adversely affects the performance of the battery. When the molecular weight is too large, dispersion of the polyether polyol in the positive electrode slurry is not desirable. Therefore, the weight-average molecular weight of the polyether polyol should be controlled within the foregoing range. In this application, the weight-average molecular weight of the polyether polyol can be measured using gel permeation chromatography.

In some embodiments, a mass ratio of the polyether polyol to the positive electrode active material ranges from 0.0005 to 0.040, optionally ranges from 0.001 to 0.02, more optionally ranges from 0.001 to 0.01, and most optionally ranges from 0.001 to 0.007.

The mass ratio of the polyether polyol to the positive electrode active material ranges from 0.0005 to 0.040. When the ratio is too small, cracking of the positive electrode plate occurs at a high coating mass, and when the ratio is too large, the performance of the battery is adversely affected.

In some embodiments, the positive electrode active material is selected from at least one of lithium iron phosphate, lithium manganese iron phosphate, lithium manganese oxide, lithium cobalt oxide, lithium nickel cobalt manganese oxide, lithium nickel cobalt aluminate, lithium nickel oxide, or a mixture thereof.

Theoretically, for the positive electrode of the secondary battery, any positive electrode active material for batteries well-known in the art can be used in this application. For example, the positive electrode active material may include at least one of the following materials: olivine-structured lithium-containing phosphate, lithium transition metal oxide, and respective modified compounds thereof. However, this application is not limited to such materials, and may alternatively use other conventional well-known materials that can be used as positive electrode active materials for batteries. One type of these positive electrode active materials may be used alone, or two or more of them may be used in combination. Examples of the lithium transition metal oxide may include but are not limited to at least one of lithium cobalt oxide (for example, $LiCoO_2$), lithium nickel oxide (for example, $LiNiO_2$), lithium manganese oxide (for example, $LiMnO_2$ and $LiMn_2O_4$), lithium nickel cobalt oxide, lithium manganese cobalt oxide, lithium nickel manganese oxide, lithium nickel cobalt manganese oxide (for example, $LiNi_{1/3}Co_{1/3}Mn_{1/3}O_2$ (NCM333 for short), $LiNi_{0.5}Co_{0.2}Mn_{0.3}O_2$ (NCM523 for short), $LiNi_{0.5}Co_{0.25}Mn_{0.25}O_2$ (NCM211 for short), $LiNi_{0.6}Co_{0.2}Mn_{0.2}O_2$ (NCM622 for short), and $LiNi_{0.8}Co_{0.1}Mn_{0.1}O_2$ (NCM811 for short)), lithium nickel cobalt aluminum oxide (for example, $LiNi_{0.85}Co_{0.15}Al_{0.05}O_2$), and modified compounds thereof. Examples of the olivine-structured lithium-containing phosphate may include but are not limited to at least one of lithium iron phosphate (for example, $LiFePO_4$ (LFP for short)), a composite material of lithium iron phosphate and carbon, lithium manganese phosphate (for example, $LiMnPO_4$), composite materials of lithium manganese phosphate and carbon, lithium manganese iron phosphate, and composite materials of lithium manganese iron phosphate and carbon.

However, the inventors of this application have found that when the positive electrode active material is at least one of lithium iron phosphate, lithium manganese iron phosphate, lithium manganese oxide, lithium cobalt oxide, lithium nickel cobalt manganese oxide, lithium nickel cobalt aluminate, lithium nickel oxide, or a mixture thereof, the addition of the polyether polyol can better achieve the effects of, for example, improving the flexibility of the electrode plate and increasing the maximum coating mass of the electrode plate.

In some embodiments, a gel state factor G of the positive electrode slurry ranges from 0 to 1, and optionally ranges from 0 to 0.3;

where G=(m1−m2)/m1, the slurry is determined not to be gelled when G ranges from 0 to 0.3, and the slurry is determined to be gelled when G is greater than 0.3;

m1 is a mass of a positive electrode slurry obtained after 2 kg of an initial positive electrode slurry is filtered for 10 minutes using a 100-mesh filter; and m2 is a mass of a positive electrode slurry obtained after 2 kg of a positive electrode slurry that has been left standing for 48 hours is filtered for 10 minutes using a 100-mesh filter; where the positive electrode slurry used for determining m1 and the positive electrode slurry used for determining m2 are from the same batch of positive electrode slurry.

The positive electrode slurry obtained by filtration after the positive electrode slurry has been left standing for 48 h has a mass more similar to the initially obtained mass of the positive electrode slurry and has a smaller G-value, indicating that the slurry is less prone to be gelled and the slurry has a better state. The anti-gelation performance of the positive electrode slurry described in this application is excellent.

A second aspect of this application provides a positive electrode plate including:

a positive electrode current collector; and a positive electrode film layer on at least one surface of the positive electrode current collector, where the positive electrode film layer includes the positive electrode slurry according to the first aspect of this application. As mentioned above, with the polyether polyol added, this application allows the maximum coating mass of the positive electrode plate to be increased, which is also manifested in an increase in the maximum mass of the positive electrode film layer. In some embodiments, the positive electrode film layer has a mass per unit area on the electrode plate ranging from 13 mg/cm$^2$ to 35 mg/cm$^2$, optionally ranging from 22 mg/cm$^2$ to 31 mg/cm$^2$, and more optionally ranging from 25 mg/cm$^2$ to 29 mg/cm$^2$, and the mass is a mass of a positive electrode film layer on a single surface of the electrode plate. If the positive electrode film layer is provided on each of two surfaces of the positive electrode plate, the positive electrode film layer has a mass per unit area on the electrode plate that is twice the foregoing range, to be specific, ranging from 26 mg/cm$^2$ to 70 mg/cm$^2$, optionally ranging from 44 mg/cm$^2$ to 62 mg/cm$^2$, and more optionally ranging from 50 mg/cm$^2$ to 58 mg/cm$^2$, and the mass is a mass of a positive electrode film layer on the two surfaces of the electrode plate.

In some embodiments, after the polyether polyol described in this application is added, the maximum coating mass per unit area on the positive electrode plate is up to 35 mg/cm$^2$ in terms of the mass of the positive electrode film layer on a single surface of the electrode plate.

The maximum coating mass per unit area described in this application can be determined in the following manner:

(1) when the positive electrode slurry is applied, testing whether cracking occurs in the coating process, and if no cracking occurs, continuing with the test in (2);

(2) in cold pressing, determining whether fracture occurs in the cold pressing process, and if no fracture occurs, continuing with the test in (3); and (3) performing the flexibility test of the positive electrode plate described in this application, where a maximum coating mass corresponding to the test result of below flexibility level 2 is the maximum coating mass described in this application.

In other words, in the process of preparing the electrode plate, the maximum coating mass that can allow no cracking in coating, no fracture in cold pressing, and a flexibility test result of below level 2 is the maximum coating mass.

The foregoing manner is used in the embodiments of this application to determine the maximum coating mass per unit area.

When the mass per unit area of the positive electrode film layer on the electrode plate is too small, the electrode plate has undesirable uniformity; and when the mass per unit area of the positive electrode film layer on the electrode plate is too large, severe cracking occurs in the electrode plate coating process and the fabrication has to be interrupted. In this application, the mass per unit area of the positive electrode film layer on the electrode plate is limited within the foregoing range so as to ensure that the best effect can be achieved within this range.

The positive electrode current collector includes two opposite surfaces in its thickness direction, and the positive electrode film layer is disposed on either or both of the two opposite surfaces of the positive electrode current collector.

In some embodiments, the positive electrode current collector may be a metal foil current collector or a composite current collector. For example, an aluminum foil may be used as the metal foil. The composite current collector may include a polymer material matrix and a metal layer formed on at least one surface of the polymer material matrix. The composite current collector may be formed by forming a metal material (aluminum, aluminum alloy, nickel, nickel alloy, titanium, titanium alloy, silver, silver alloy, or the like) on a polymer material matrix (for example, matrices of polypropylene (PP), polyethylene terephthalate (PET), polybutylene terephthalate (PBT), polystyrene (PS), and polyethylene (PE)).

In the positive electrode plate, a mass percentage of the positive electrode active material in the positive electrode film layer ranges from 90% to 97% based on the mass of the positive electrode film layer. Such percentage can be measured using an X-ray energy dispersive spectrometry (EDS) or inductively coupled plasma spectrometry (ICP). When the mass percentage is too low, the energy density of the battery prepared is too low to meet the battery capacity requirements; and when the mass percentage is too high, the binder and the conductive agent are insufficient, resulting in poor battery performance.

In the positive electrode plate, a mass percentage of the binder in the positive electrode film layer ranges from 2% to 5% based on the total mass of the positive electrode film layer. For example, the binder may include at least one of polyvinylidene fluoride (PVDF), polytetrafluoroethylene (PTFE), vinylidene fluoride-tetrafluoroethylene-propylene terpolymer, vinylidene fluoride-hexafluoropropylene-tetrafluoroethylene terpolymer, tetrafluoroethylene-hexafluoropropylene copolymer, or fluorine-containing acrylic resin. Existing conventional positive electrode plates in which a binder of a specific crystallinity or similar crystallinity is used are more brittle after suffering from coating and drying to form a film, and the electrode plates are prone to cracking under stress. However, the positive electrode plate of this application using the binder with the same crystallinity does not crack.

In some embodiments, the positive electrode film layer further optionally includes a conductive agent. For example, the conductive agent may include at least one of superconducting carbon, acetylene black, carbon black, Ketjen black, carbon dots, carbon nanotubes, graphene, and carbon nanofiber.

In some embodiments, the positive electrode plate may be prepared in the following manner: the foregoing constituents used for preparing the positive electrode plate, for example, the positive electrode active material, the conductive agent, the binder, and any other constituent, are dispersed in a solvent (for example, N-methylpyrrolidone) to form a positive electrode slurry; and the positive electrode slurry is applied onto the positive electrode current collector, followed by processes such as drying and cold pressing to obtain the positive electrode plate.

The positive electrode plate described in this application has good flexibility and a significantly increased coating mass. Application of such positive electrode plate to a secondary battery, for example, adding it directly to the positive electrode slurry during preparation, can significantly improve the energy density of the battery.

In some optional embodiments, the positive electrode film layer may include two sublayers. The sublayers are parallel to the positive electrode current collector and superimposed with each other. A ratio of a mass percentage of the polyether polyol in the sublayer closer to the positive electrode current collector (that is, the sublayer close to the current collector) to a mass percentage of the polyether polyol in the sublayer farther from the positive electrode current collector (that is, the sublayer far from the current collector) ranges from 0 to 80, and optionally ranges from 0 to 40. In some optional embodiments, in the sub-layer close to the current collector, the mass ratio of the polyether polyol to the positive electrode active material ranges from 0 to 0.04; and in the sub-layer away from the current collector, the mass ratio of the polyether polyol to the positive electrode active material ranges from 0.0005 to 0.004.

Under the condition that the coating mass is 23 mg/cm$^2$ or above, as compared with single thick coating, in multiple coatings, the material cost of the flexible additive can be reduced, and the polyether polyol described in this application can function better without affecting the electrical performance of the secondary battery.

Optionally, in preparing a positive electrode film layer with two sublayers, two positive electrode slurries containing different amounts of polyether polyol are first prepared, one slurry is applied on the current collector and then dried, and in turn the other slurry is applied and dried.

In some embodiments, under the condition that flexibility of the positive electrode plate is measured using a winding needle,
- when a diameter R of the winding needle is less than or equal to 3.0 mm, the positive electrode plate has no cracks produced; or
- when a diameter R of the winding needle is equal to 3.0 mm, the positive electrode plate has cracks produced, but when the diameter R of the winding needle is equal to 4.0 mm, the positive electrode plate has no cracks produced.

In any embodiment, in the positive electrode plate according to this application, when the flexibility of the positive electrode plate is measured using a winding needle, an electrode plate sample with a width×length of 50 mm×100 mm is prepared and then wound on a specially made winding needle. The cracking of the electrode plate is observed through both visual and microscopic inspection. The flexibility level is determined in the following method: assuming the diameter of the winding needle to be R:
- if the electrode plate has no cracks produced when R≤3.0 mm, determining the flexibility level to be flexibility level 1;
- if the electrode plate has cracks produced when R=3.0 mm and has no cracks produced when R=4.0 mm, determining the flexibility level to be flexibility level 2;
- if the electrode plate has no cracks produced when R=4.0 mm and has cracks produced when R=5.0 mm, determining the flexibility level to be flexibility level 3;
- if the electrode plate has no cracks produced when R=5.0 mm and has cracks produced when R=6.0 mm, determining the flexibility level to be flexibility level 4; and
- if the electrode plate has no cracks produced when R=6.0 mm and has cracks produced when R=7.0 mm, determining the flexibility level to be flexibility level 5.

The winding needle is prepared as follows:
- 60 mm of samples are cut out of the 304 stainless steel bars with conventional diameters of 3.0 mm, 4.0 mm, 5.0 mm, 6.0 mm, and 7.0 mm and then welded on a steel plate of 150 mm×300 mm for fixing to obtain the winding needle.

When no cracking of the electrode plate occurs, a smaller diameter of the winding needle used indicates better flexibility of the electrode plate. Conversely, when cracking of the electrode plate occurs, a larger diameter of the winding needle used indicates worse flexibility of the electrode plate.

In the cold pressing process, the hydrogen bonds formed are broken and the flexible main chains are stretched. However, the addition of the polyether polyol described in this application can reduce the cold pressing pressure, thereby reducing cracks and the risk of strip breakage.

In some embodiments, the positive electrode plate has an infiltration increase rate I ranging from 2% to 20%, optionally ranging from 6% to 15%;
where $I=(I2-I1)/I1\times100\%$;
- I2 is an infiltration rate of the positive electrode plate in an electrolyte; and
- I1 is an infiltration rate of a positive electrode plate containing no polyether polyol in an electrolyte;
- where the positive electrode plate used for determining I1 is the same as the positive electrode plate used for determining I2, differing only in that the positive electrode plate used for determining I1 contains no polyether polyol, and the positive electrode plate used for determining I2 contains the polyether polyol.

The electrode plate with high infiltrability can realize good infiltration in the electrolyte and electrolyte retention, thus realizing effective infiltration into the electrode plate of the cell, avoiding inadequate infiltration into the electrode plate, improving the efficiency of electrolyte injection of the cell and the infiltration into the electrode plate during the cycling, and thus effectively improving the performance of battery products. The positive electrode plate described in this application has quite high infiltrability in the electrolyte.

A third aspect of this application provides a secondary battery including the positive electrode plate according to the second aspect of this application or a positive electrode plate obtained from the positive electrode slurry according to the first aspect of this application. The energy density of the secondary battery described in this application is significantly improved. In addition, the total material cost is reduced in the preparation of the battery.

The secondary battery, battery module, battery pack, and electric apparatus of this application are described below.

Secondary Battery

Normally, the secondary battery includes a positive electrode plate, a negative electrode plate, an electrolyte, and a separator. In a charge and discharge process of the battery, active ions are intercalated and deintercalated between the positive electrode plate and the negative electrode plate. The electrolyte conducts ions between the positive electrode plate and the negative electrode plate. The separator is disposed between the positive electrode plate and the negative electrode plate to mainly prevent a short circuit between positive and negative electrodes and to allow the ions to pass through.

[Positive Electrode Plate]

The positive electrode plate according to the second aspect of this application or a positive electrode plate prepared using the positive electrode slurry according to the first aspect of this application is used.

[Negative Electrode Plate]

The negative electrode plate includes a negative electrode current collector and a negative electrode film layer disposed on at least one surface of the negative electrode current collector, where the negative electrode film layer includes a negative electrode active material.

For example, the negative electrode current collector includes two opposite surfaces in its thickness direction, and the negative electrode film layer is disposed on either or both of the two opposite surfaces of the negative electrode current collector.

In some embodiments, the negative electrode current collector may be a metal foil current collector or a composite current collector. For example, for the metal foil, a copper foil may be used. The composite current collector may include a polymer material matrix and a metal layer formed on at least one surface of the polymer material matrix. The composite current collector may be formed by forming a metal material (copper, copper alloy, nickel, nickel alloy, titanium, titanium alloy, silver, silver alloy, or the like) on a polymer material matrix (for example, matrices of polypropylene (PP), polyethylene terephthalate (PET), polybutylene terephthalate (PBT), polystyrene (PS), and polyethylene (PE)).

In some embodiments, the negative electrode active material may be a well-known negative electrode active material used for a battery in the art. For example, the negative electrode active material may include at least one of the following materials: artificial graphite, natural graphite, soft carbon, hard carbon, a phosphorus-based material, a tin-based material, lithium titanate, or the like. The phosphorus-based material may be selected from at least one of elemental phosphorus, phosphorus oxide compound, phosphorus carbon compound, phosphorus nitrogen compound, and phosphorus alloy. The tin-based material may be selected from at least one of elemental tin, tin-oxygen compound, and tin alloy. However, this application is not limited to these materials, but may use other conventional materials that can be used as negative electrode active materials for batteries instead. One of these negative electrode active materials may be used alone, or two or more of them may be used in combination.

In some embodiments, the negative electrode film layer further optionally includes a binder. The binder may be selected from at least one of styrene-butadiene rubber (SBR), polyacrylic acid (PAA), polyacrylic acid sodium (PAAS), polyacrylamide (PAM), polyvinyl alcohol (PVA), sodium alginate (SA), polymethacrylic acid (PMAA), and carboxymethyl chitosan (CMCS).

In some embodiments, the negative electrode film layer further optionally includes a conductive agent. The conductive agent may be selected from at least one of superconducting carbon, acetylene black, carbon black, Ketjen black, carbon dots, carbon nanotubes, graphene, and carbon nanofiber.

In some embodiments, the negative electrode film layer may further optionally include other promoters such as a thickener (for example, sodium carboxymethyl cellulose (CMC-Na)).

In some embodiments, the negative electrode plate may be prepared in the following manner: the foregoing constituents used for preparing the negative electrode plate, for example, the negative electrode active material, the conductive agent, the binder, and any other constituent, are dispersed in a solvent (for example, deionized water) to form a negative electrode slurry; and the negative electrode slurry is applied onto the negative electrode current collector, followed by processes such as drying and cold pressing to obtain the negative electrode plate.

[Electrolyte]

The electrolyte conducts ions between the positive electrode plate and the negative electrode plate. The electrolyte is not specifically limited to any particular type in this application, and may be selected based on needs. For example, the electrolyte may be selected from at least one of a solid electrolyte and a liquid electrolyte (that is, an electrolyte solution).

In some embodiments, the electrolyte is a liquid electrolyte. The liquid electrolyte includes an electrolytic salt and a solvent.

In some embodiments, the electrolytic salt may be one or more of lithium hexafluorophosphate ($LiPF_6$), lithium tetrafluoroborate ($LiBF_4$), lithium perchlorate ($LiClO_4$), lithium hexafluoroarsenate ($LiAsF_6$), lithium bis(fluorosulfonyl)imide (LiFSI), lithium bistrifluoromethanesulfonimide (LiTFSI), lithium trifluoromethanesulfonate (LiTFS), lithium difluoro(oxalato)borate (LiDFOB), lithium dioxalate borate (LiBOB), lithium difluorophosphate ($LiPO_2F_2$), lithium difluoro(dioxalato)phosphate (LiDFOP), and lithium tetrafluoro oxalato phosphate (LiTFOP).

In some embodiments, the solvent may be selected from one or more of ethylene carbonate (EC), propylene carbonate (PC), ethyl methyl carbonate (EMC), diethyl carbonate (DEC), dimethyl carbonate (DMC), dipropyl carbonate (DPC), methyl propyl carbonate (MPC), ethyl propyl carbonate (EPC), butylene carbonate (BC), fluoroethylene carbonate (FEC), methyl formate (MF), methyl acetate (MA), ethyl acetate (EA), propyl acetate (PA), methyl propionate (MP), ethyl propionate (EP), propyl propionate (PP), methyl butyrate (MB), ethyl butyrate (EB), 1,4-butyrolactone (GBL), sulfolane (SF), methyl sulfonyl methane (MSM), methyl ethyl sulfone (EMS), and diethyl sulfone (ESE).

In some embodiments, the electrolyte further optionally includes an additive. For example, the additive may include a negative electrode film-forming additive, or may include a positive electrode film-forming additive, or may include an additive capable of improving some performance of the battery, for example, an additive for improving overcharge performance of the battery, an additive for improving high-temperature performance of the battery, or an additive for improving low-temperature performance of the battery.

[Separator]

In some embodiments, the secondary battery further includes a separator. The separator is disposed between the positive electrode plate and the negative electrode plate to provide separation. The separator is not limited to any particular type in this application, and may be any well-known porous separator with good chemical stability and mechanical stability.

In some embodiments, a material of the separator may be selected from at least one of glass fiber, non-woven fabric, polyethylene, polypropylene, and polyvinylidene fluoride. The separator may be a single-layer film or a multi-layer composite film, and is not particularly limited. When the separator is a multi-layer composite film, all layers may be made of same or different materials, which is not particularly limited.

[Outer Package]

In some embodiments, the secondary battery may include an outer package for packaging the positive electrode plate, the negative electrode plate, and an electrolyte. In an example, the positive electrode plate, the negative electrode plate, and the separator may be laminated or wound to form a battery cell of a laminated structure or a battery cell of a wound structure, and the battery cell is packaged in an outer package. The electrolyte may be a liquid electrolyte, and the liquid electrolyte infiltrates into the battery cell. There may be one or more battery cells in the secondary battery, and the quantity can be adjusted based on needs.

In an embodiment, this application provides an electrode assembly. In some embodiments, the positive electrode plate, the negative electrode plate, and the separator may be made into an electrode assembly through winding or lamination. The outer package may be used for packaging the foregoing electrode assembly and electrolyte.

In some embodiments, the outer package of the secondary battery may alternatively be a soft pack, for example, a soft pouch. A material of the soft pack may be plastic, for example, may include one or more of polypropylene (PP), polybutylene terephthalate (PBT), polybutylene succinate (PBS), and the like. In some embodiments, the outer package of the secondary battery may be a hard shell, for example, a hard plastic shell, an aluminum shell, or a steel shell.

Preparation Method of Secondary Battery

In an embodiment, this application provides a preparation method of secondary battery, where the negative electrode plate according to this application or a negative electrode plate prepared according to the method of this application is used.

The preparation of the secondary battery may further include the step of assembling the negative electrode plate, positive electrode plate, and electrolyte of this application to form the secondary battery. In some embodiments, the positive electrode plate, the separator, and the negative electrode may be wound or laminated in sequence such that the separator is located between the positive electrode plate and the negative electrode plate for separation to obtain a battery cell. The battery cell is placed into an outer package, the liquid electrolyte is injected, and the package is then sealed, such that a secondary battery is obtained.

In some embodiments, the preparation of the secondary battery may further include the step of preparing a positive electrode plate. In an example, a positive electrode active material, a conductive agent, and a binder may be dispersed in a solvent (for example, N-methylpyrrolidone, NMP for short) to form a uniform positive electrode slurry, and the positive electrode slurry is applied on a positive electrode current collector, and processes such as drying and cold pressing are performed to obtain a positive electrode plate.

In some embodiments, the preparation of the secondary battery includes the step of preparing a negative electrode plate according to the method of this application.

This application does not impose any special limitations on a shape of the secondary battery, and the secondary battery may be cylindrical, rectangular, or of any other shapes.

In some embodiments, this application provides an electric apparatus, a battery module, or a battery pack, where the electric apparatus, battery module, or battery pack includes the secondary battery according to this application or a secondary battery prepared according to the method of this application.

In some embodiments, the secondary battery may be assembled into a battery module, and the battery module may include one or more secondary batteries. The specific quantity may be chosen by persons skilled in the art according to use and capacity of the battery module.

In some embodiments, the battery module may be further assembled into a battery pack, and the battery pack may include one or more battery modules. The specific quantity may be chosen by persons skilled in the art according to use and capacity of the battery pack.

In addition, this application further provides an electric apparatus. The electric apparatus includes at least one of the secondary battery, the battery module, or the battery pack provided in this application. The secondary battery, the battery module, or the battery pack may be used as a power source for the electric apparatus or an energy storage unit of the electric apparatus. The electric apparatus may include a mobile device (for example, a mobile phone or a notebook computer), an electric vehicle (for example, a battery electric vehicle, a hybrid electric vehicle, a plug-in hybrid electric vehicle, an electric bicycle, an electric scooter, an electric golf vehicle, or an electric truck), an electric train, a ship, a satellite system, an energy storage system, or the like, but is not limited thereto. In another example, the apparatus may be a mobile phone, a tablet computer, a notebook computer, or the like. The apparatus usually requires to be light and thin, and a secondary battery may be used as a power source. The secondary battery, the battery module, or the battery pack may be selected for the electric apparatus based on requirements for using the electric apparatus.

Therefore, this application provides a battery module including the secondary battery according to this application.

In addition, this application further provides a battery pack including the foregoing battery module.

This application further provides an electric apparatus including at least one of the secondary battery, the battery module, or the battery pack according to this application.

EXAMPLES

The following describes examples of this application. The examples described below are illustrative and only used for explaining this application, and cannot be construed as limitations on this application. Examples whose technical solutions or conditions are not specified are made in accordance with technical solutions or conditions described in literature in the field or made in accordance with product instructions. The reagents or instruments used are all conventional products that are commercially available if no manufacturer is indicated.

Example 1

Step 1: Preparation of Polyether Polyol 26.68 g of sodium hydroxide serving as a catalyst, 19.98 g of glycerol serving as a regulator, 439 g of bisphenol A serving as an initiator, and 3557 g of propylene oxide were added into an autoclave for reacting at 158° C. for 30 h, during which the vacuum degree was not greater than 0.1 MPa, to obtain crude polyether polyol. The crude polyether polyol was neutralized with oxalic acid to a pH value of 7.0 to 7.2, vacuum degassed for 1 h, adsorbed by activated carbon for 1 h, and vacuum filtered to obtain finished polyether polyol with a weight-average molecular weight of 20,000. The weight-average molecular weight was determined by gel permeation chromatography.

Step 2: Preparation of Positive Electrode Slurry 5477 g of a positive electrode active material (lithium iron phosphate), 62.37 g of a conductive agent (conductive carbon black Super P), and 113.4 g of a binder PVDF (see Table 2 for specific amount) were mixed for 30 min. Then, the resulting mixture was added to 3330 g of NMP and stirred for 180 min for uniform dispersion. Finally, the resulting mixture was added with 17.01 g of polyether polyol prepared in step 1 and then fully stirred for 60 min to form a uniform positive electrode slurry.

Step 3: Preparation of Positive Electrode Plate

The positive electrode slurry prepared in step 2 was applied onto two surfaces of the positive electrode current collector aluminum foil, followed by drying and cold pressing, to obtain a positive electrode plate. A series of performance tests were performed on the positive electrode plate with a maximum coating mass per unit area of 31 mg/cm$^2$.

Step 4: Preparation of Negative Electrode Plate

A negative electrode active material (graphite), a conductive agent (Super-P), a binder (SBR), and a thickener (CMC) were mixed and fully stirred at a mass ratio of 96.2:0.8:1.8:1.2 in an appropriate amount of deionized water to form a uniform negative electrode slurry. The negative electrode slurry was applied onto two surfaces of a current collector copper foil, followed by drying and cold pressing, to obtain a negative electrode plate.

Step 5: Preparation of Electrolyte

Ethylene carbonate (EC), ethyl methyl carbonate (EMC), and diethyl carbonate (DEC) were mixed at a volume ratio of 1:1:1, and then LiPF$_6$ was uniformly dissolved in the foregoing solution to obtain an electrolyte, where a concentration of LiPF$_6$ was 1 mol/L.

Step 6: Separator

A polyethylene (PE) film was used.

Step 7: Preparation of Secondary Battery

The foregoing positive electrode plate, separator, and negative electrode plate were stacked in sequence and wound to obtain an electrode assembly. The electrode assembly was placed in an outer package, the foregoing electrolyte was added, and steps such as packaging, standing, formation, and aging were performed to obtain a secondary battery of Example 1. A hard shell with the length×width×height of 148 mm×28.5 mm×97.5 mm was chosen as the outer package.

Examples 2 to 9

The secondary batteries of Examples 2 to 9 were prepared in a manner similar to that of Example 1, with the difference lying in the preparation of polyether polyol in step 1. See Table 1 for details.

TABLE 1

Preparation of polyether polyol

| No. | Initiator Type | Initiator Amount (g) | Amount of propylene oxide (g) | Amount of NaOH (g) | Reacting time (h) |
|---|---|---|---|---|---|
| Example 1 | Bisphenol A | 439 | 3557 | 26.68 | 30 |
| Example 2 | Bisphenol A | 439 | 3557 | 17.79 | 7 |
| Example 3 | Bisphenol A | 439 | 3557 | 18.50 | 10 |
| Example 4 | Bisphenol A | 439 | 3557 | 19.56 | 15 |
| Example 5 | Bisphenol A | 439 | 3557 | 28.46 | 38 |
| Example 6 | Bisphenol A | 439 | 3557 | 32.01 | 45 |
| Example 7 | Bisphenol A | 439 | 3557 | 10.67 | 3 |
| Example 8 | Bisphenol S | 439 | 1057 | 15.75 | 32 |
| Example 9 | 4,4'-methylene bis(2-methylphenol) | 439 | 1320 | 15.75 | 28 |

Examples 10 to 16

The secondary batteries of Examples 11 to 16 were prepared in a manner similar to that of Example 1, with the difference lying in the amount of positive electrode active material lithium iron phosphate and the amount of polyether polyol in step 2. See Table 2 for details.

TABLE 2

Materials used in preparation of positive electrode slurry and amount thereof

| Preparation example | Lithium iron phosphate (g) | Polyether polyol (g) |
|---|---|---|
| Example 1 | 5477 | 17.01 |
| Example 10 | 5491 | 2.84 |
| Example 11 | 5324 | 170.10 |
| Example 12 | 5489 | 5.67 |
| Example 13 | 5381 | 113.40 |
| Example 14 | 5455 | 39.69 |
| Example 15 | 5493 | 1.13 |
| Example 16 | 5211 | 283.50 |

Comparative Example 1

The secondary battery of Comparative Example 1 was prepared in a manner similar to that of Example 1, with the difference lying in that no polyether polyol was added, in other words, there was no step 1 and no polyether polyol was added in step 2.

Test for Slurry Parameters

1. Gel State Factor of Positive Electrode Slurry

The gel state of the positive electrode slurry was evaluated in the following method.

The gel state factor of the positive electrode slurry was denoted by G, G=|(m2−m1)/m1|, where m1 is a mass of a positive electrode slurry obtained after 2 kg of an initial positive electrode slurry is filtered for 10 minutes using a 200-mesh filter; and m2 is a mass of a positive electrode slurry obtained after 2 kg of a positive electrode slurry that has been left standing for 48 hours is filtered for 10 minutes using a 200-mesh filter; where the positive electrode slurry used for determining m1 and the positive electrode slurry used for determining m2 are from the same batch of positive electrode slurry.

If G ranged from 0 to 0.3, the slurry was determined not to be gelled; and G>0.3, the slurry was determined to be gelled.

Test for Parameters of Positive Electrode Plate

1. Test for Flexibility of Positive Electrode Plate

The flexibility of the positive electrode plate was evaluated using a winding needle, and the test method was as follows:

An electrode plate sample with a width×length of 50 mm×100 mm was prepared and then wound on a specially made winding needle. The cracking of the electrode plate was observed through both visual and microscopic inspection.

Figure 5:
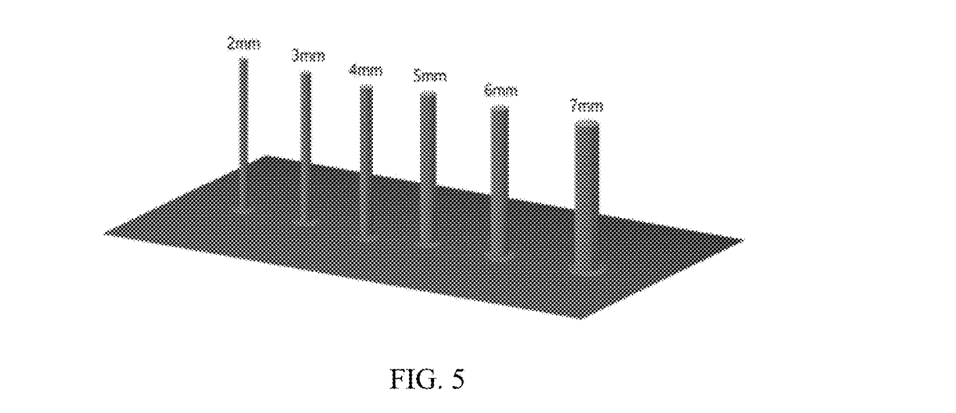
FIG. 5 is a schematic diagram of a winding needle used in flexibility test of a positive electrode plate of this application.

Specially made winding needle:

60 mm of samples were cut out of the 304 stainless steel bars with conventional diameters of 3.0 mm, 4.0 mm, 5.0 mm, 6.0 mm, and 7.0 mm and then welded on a steel plate of 150 mm×300 mm for fixing to obtain the winding needle, as shown in FIG. 5.

The flexibility level was determined in the following method:

assuming the diameter of the winding needle to be R:

if the electrode plate has no cracks produced when R≤3.0 mm, determining the flexibility level to be flexibility level 1;

if the electrode plate has cracks produced when R=3.0 mm and has no cracks produced when R=4.0 mm, determining the flexibility level to be flexibility level 2;

if the electrode plate has no cracks produced when R=4.0 mm and has cracks produced when R=5.0 mm, determining the flexibility level to be flexibility level 3;

if the electrode plate has no cracks produced when R=5.0 mm and has cracks produced when R=6.0 mm, determining the flexibility level to be flexibility level 4; and if the electrode plate has no cracks produced when R=6.0 mm and has cracks produced when R=7.0 mm, determining the flexibility level to be flexibility level 5.

2. Infiltration Increase Rate of Positive Electrode Plate

The infiltration increase rate of the positive electrode plate is expressed as I, and $I=(I2-I1)/I1 =100\%$ where I2 is an infiltration rate of the positive electrode plate in an electrolyte; and I1 is an infiltration rate of a positive electrode plate containing no polyether polyol in an electrolyte;

where the positive electrode plate used for determining I1 was the same as the positive electrode plate used for determining I2, differing only in that the positive electrode plate used for determining I1 contained no polyether polyol, and the positive electrode plate used for determining I2 contained the polyether polyol.

The procedures for the determination of I1 and I2 were as follows:

The absorption rate of the electrode plate was tested by using the capillary method. An electrode plate of a size larger than or equal to 50 mm×50 mm was prepared, with a flat surface and with no folds, no film peeling, and no powder falling; a capillary tube with an inner diameter d of 100 μm was chosen and then polished with sandpaper until the opening was neat; the capillary tube suctioned up the electrolyte until h was equal to 5 mm, that is, the electrolyte height was controlled to be 5 mm; the capillary tube was put under the microscope such that it was in contact with the electrode plate; as the electrolyte level of the capillary tube dropped, the time was recorded with a stopwatch; and after the electrolyte level had dropped to zero, the absorption time was read and the data t was recorded. Then the infiltration rate of the electrolyte was calculated from $\pi \times (d/2)^2 \times h \times \rho/t$, where $\pi$ is 3.14 and $\rho$ is the density of the electrolyte.

3. Measurement of Coating Mass Per Unit Area

An uncoated aluminum foil and the positive electrode plate that had been dried in the coating process (where in the positive electrode plate, two sides of the positive electrode current collector were coated) were prepared, and 15 small discs with an area of 1540.25 mm² were punched for each of the former two. The coating mass per unit area can be obtained by subtracting the average mass of the uncoated small aluminum foil discs from the average mass of the small electrode plate discs and then dividing the result difference by 2.

The term "single surface" refers to coating on only one surface of the current collector, and is a concept different from the number of "sublayers" described earlier in this application. The maximum coating mass per unit area in the table refers to the coating mass on a single surface.

Data of the coating masses of examples in the table of this application refers to data of the maximum coating mass per unit area on a single surface, and the performance of the electrode plate and the performance of the battery are both measured at the maximum coating mass.

The maximum coating mass per unit area is determined in a method described in the previous sections.

Battery-Related Performance Test

1. Energy Density Test

The battery prepared in each example and comparative example was weighed to obtain the mass of the entire battery; after the battery suffered from capacity formation, the battery was left standing for 10 min at 25° C., and charged to 100% SOC at 0.33C, and then the battery was left standing for 10 min after suffering from low current depolarization, and discharged to 0% SOC at 0.33. The capacity obtained at this point was the 0.33C capacity of the battery. After left standing for 30 min, the battery was charged to 100% SOC, and then after left standing for 30 min, the battery was discharged at a constant current of 0.01C for 30 min. The voltage remained constant in a time, and this constant value was the charging and discharging platform, namely, a platform voltage. Finally, the mass energy density of the battery was calculated: battery mass energy density=battery capacity×discharge platform voltage/mass of entire battery, in a basic unit of Wh/kg (Watt-hour/kg).

2. Determination of Direct Current Resistance (Direct Current Resistance, DCR for Short)

The capacity test for the battery prepared in each example was carried out at 25° C. The capacity test method was as above. The battery was charged at a constant voltage of 0.05C, left standing for 60 min, discharged at 0.33C to 50% SOC, left standing for 60 min, discharged at 0.33C to 20% SOC, left standing for 60 min, and discharged at 0.33C to 0% SOC. The open circuit voltage was tested at 0% SOC, and the DCR data in 30s was compiled.

All tests were performed at the maximum coating masses for all examples and comparative examples.

See Tables 3 to 5 for test results. "/" in the table means that this item was not present, not added, or not measured.

TABLE 3

Comparison of cases with polyether polyol added and with no polyether polyol added

| | No. | Example 1 | Comparative Example 1 |
|---|---|---|---|
| Positive electrode slurry | Molecular weight of polyether polyol | 20000 | / |
| | Mass ratio of polyether polyol to positive electrode active material | 0.003 | / |
| | Gel state factor G | 0.1 | 0.6 |
| Layer structure of positive electrode plate | Number of positive electrode film layers on one surface of current collector | Single layer | Single layer |
| | Diameter of winding needle (R/mm) | ≤3 | 6 |
| | Maximum coating mass per unit area (mg/cm²) | 31 | 22 |
| | Infiltration increase rate I | 15% | / |
| Battery performance | Energy density (Wh/kg) | 197 | 187 |
| | DCR (mΩ) | 2.0 | 3.5 |

It can be seen from Table 3 that compared with Comparative Example 1 in which no polyether polyol is added, the positive electrode slurry added with polyether polyol in Example 1 has a 41% increase in coating mass per unit area and a 5% increase in energy density, in other words, the battery performance has been significantly improved.

TABLE 4

Test results of Examples 1 to 9

| | No. | Example 1 | Example 2 | Example 3 | Example 4 | Example 5 | Example 6 | Example 7 | Example 8 | Example 9 |
|---|---|---|---|---|---|---|---|---|---|---|
| Positive electrode slurry | Molecular weight of polyether polyol | 20000 | 1000 | 2000 | 4000 | 40000 | 60000 | 500 | 20000 | 20000 |
| | Mass ratio of polyether polyol to positive electrode active material | 0.003 | 0.003 | 0.003 | 0.003 | 0.003 | 0.003 | 0.003 | 0.003 | 0.003 |
| | Gel state factor G | 0.1 | 0.12 | 0.12 | 0.13 | 0.2 | 1 | 0.4 | 0.11 | 0.12 |
| Layer structure of positive electrode plate | Number of positive electrode film layers on one surface of current collector | Single layer | Single layer | Single layer | Single layer | Single layer | Single layer | Single layer | Single layer | Single layer |
| | Diameter of winding needle (R/mm) | ≤3 | ≤3 | ≤3 | ≤3 | ≤3 | ≤3 | 7 | ≤3 | ≤3 |
| | Maximum coating mass per unit area (mg/cm$^2$) | 31 | 29 | 29 | 29 | 29 | 29 | 22 | 31 | 31 |
| | Infiltration increase rate I | 15% | 10% | 12% | 11% | 13% | 10% | 2% | 15% | 15% |
| Battery performance | Energy density (Wh/kg) | 197 | 195 | 195 | 195 | 195 | 195 | 187 | 197 | 197 |
| | DCR (mΩ) | 2.0 | 2.1 | 2.3 | 2.5 | 3.0 | 12.0 | 3.5 | 2.1 | 2.3 |

It can be seen from Table 4 that the molecular weight of the polyether polyol affects the coating mass per unit area and energy density of the battery. When the molecular weight is too small, the positive electrode slurry has poor stability, physical gelation is likely to occur, and the flexibility of the positive electrode plate is not significantly improved: there is still cracking in the coating; and when the molecular weight is too large, there are more non-conducting polymers in the slurry, and consequently cross-linking in polymerization is likely to occur, resulting in gelation of the slurry, which affects the sheet resistance of the electrode plate.

TABLE 5

Test results of Examples 10 to 16

| | No | Example 1 | Example 10 | Example 11 | Example 12 | Example 13 | Example 14 | Example 15 | Example 16 |
|---|---|---|---|---|---|---|---|---|---|
| Positive electrode slurry | Molecular weight of polyether polyol | 20000 | 20000 | 20000 | 20000 | 20000 | 20000 | 20000 | 20000 |
| | Mass ratio of polyether polyol to positive electrode active material | 0.003 | 0.0005 | 0.03 | 0.001 | 0.02 | 0.007 | 0.0002 | 0.05 |
| | Gel state factor G | 0.1 | 0.32 | 0.35 | 0.15 | 0.3 | 0.18 | 0.9 | 1 |

TABLE 5-continued

Test results of Examples 10 to 16

| | No | Example 1 | Example 10 | Example 11 | Example 12 | Example 13 | Example 14 | Example 15 | Example 16 |
|---|---|---|---|---|---|---|---|---|---|
| Layer structure of positive electrode plate | Number of positive electrode film layers on one surface of current collector | Single layer | Single layer | Single layer | Single layer | Single layer | Single 1. layer | Single layer | Single layer |
| | Diameter of winding needle (R/mm) | ≤3 | 3 | ≤3 | ≤3 | ≤3 | ≤3 | 6 | 3 |
| | Maximum coating mass per unit area (mg/cm$^2$) | 31 | 28 | 31 | 30 | 31 | 31 | 22 | 31 |
| | Infiltration increase rate I | 15% | 8% | 13% | 15% | 12% | 15% | 2% | 11% |
| Battery performance | Energy density (Wh/kg) | 197 | 193 | 197 | 196 | 197 | 197 | 187 | 197 |
| | DCR (mΩ) | 2.0 | 3.2 | 3.5 | 2.3 | 3.8 | 2.7 | 3.6 | 10.7 |

It can be seen from Table 5 that the mass ratio of the polyether polyol to the positive electrode active material affects the coating mass per unit area of the electrode plate. When the mass ratio of the polyether polyol to the positive electrode active material is <0.0005, the positive electrode plate cracks at high coating mass, and the corresponding battery has low energy density; and when the mass ratio of the polyether polyol to the positive electrode active material is >0.03, the sheet resistance of the electrode plate deteriorates, and the impedance DCR of the battery is relatively high, which greatly affect the rate performance the battery.

It should be noted that this application is not limited to the foregoing embodiments. The foregoing embodiments are merely examples, and embodiments having substantially the same constructions and the same effects as the technical idea within the scope of the technical solutions of this application are all included in the technical scope of this application. In addition, without departing from the essence of this application, various modifications made to the embodiments that can be conceived by persons skilled in the art, and other manners constructed by combining some of the constituent elements in the embodiments are also included in the scope of this application.

What is claimed is:

1. A positive electrode slurry, comprising:
a positive electrode active material; and
polyether polyol, the polyether polyol having following constitutional formula:

formula 1 wherein:
$R_1$, $R_2$, $R_3$, $R_4$, $R_5$, $R_6$, $R_7$, $R_8$, $R_9$, and $R_{10}$ are each independently selected from H, a hydroxyl group, halogen, —CH$_3$, and X, wherein:
X has following constitutional formula:

—O(CH$_2$—CHR—O)$_n$D        formula 2 wherein:
n is an integer ranging from 6 to 1000;
D is H or a C$_{1-8}$ alkyl group; and
each R is independently selected from H, halogen, a hydroxyl group, a halogenated C$_{1-8}$ alkyl group, $R_{11}$, —OR$_{11}$ or R$_{11}$OR$_{12}$, wherein R$_{11}$ and R$_{12}$ are each independently selected from a straight-chain or branched-chain C$_{1-8}$ alkyl group, a phenyl group, a C$_{1-8}$ alkyl substituted phenyl group, a C$_{1-8}$ alkoxy substituted phenyl group, or a halogenated phenyl group;
at least one of $R_1$, $R_2$, $R_3$, $R_4$, $R_5$, $R_6$, $R_7$, $R_8$, $R_9$, and $R_{10}$ is X, wherein not both $R_1$ and $R_6$ are X, and not both $R_5$ and $R_{10}$ are X;
Y is selected from a group having the following constitutional formula: —O—, —S—, —CH$_2$—, —CH(CH$_3$)$_2$—, —CH(CH$_3$)(CH$_2$CH$_3$)—, —CH(CH$_3$)(Ph)-, —CH(Ph)$_2$-, —CH(COOCH$_3$)—, —CH(COOCH$_2$CH$_2$CH$_3$)—, and —S(O)$_2$—; and
a mass ratio of the polyether polyol to the positive electrode active material ranges from 0.0005 to 0.040.

2. The positive electrode slurry according to claim 1, wherein the polyether polyol has a weight-average molecular weight ranging from 1000 to 50,000.

3. The positive electrode slurry according to claim 1, wherein:
the positive electrode active material is selected from a group consisting of at least one of lithium iron phosphate, lithium manganese iron phosphate, lithium manganese oxide, lithium cobalt oxide, lithium nickel cobalt manganese oxide, lithium nickel cobalt aluminate, lithium nickel oxide, and a mixture thereof.

4. The positive electrode slurry according to claim 3, wherein:
the positive electrode active material is selected from a group consisting of at least one of lithium iron phosphate, lithium manganese iron phosphate, lithium manganese oxide, lithium nickel cobalt manganese oxide, lithium nickel cobalt aluminate, lithium nickel oxide, the a mixture thereof.

5. The positive electrode slurry according to claim 1, wherein:
a gel state factor G of the positive electrode slurry ranges from 0 to 1;
wherein:
G=1−m2/ml; and
m2/ml is a ratio of masses of the positive electrode slurry with and without being left standing for a period of time and after being filtered.

6. A positive electrode plate, comprising:
a positive electrode current collector; and
a positive electrode film layer on at least one surface of the positive electrode current collector, wherein the positive electrode film layer has a mass per unit area on a single surface of the positive electrode current collector ranging from 13 mg/cm$^2$ to 35 mg/cm$^2$, and the positive electrode film layer comprises:
a positive electrode active material; and
polyether polyol, the polyether polyol having following constitutional formula:

formula 1 wherein:
$R_1$, $R_2$, $R_3$, $R_4$, $R_5$, $R_6$, $R_7$, $R_8$, $R_9$, and $R_{10}$ are each independently selected from H, a hydroxyl group, halogen, —CH$_3$, and X, wherein:
X has following constitutional formula:

—O(CH$_2$—CHR—O)$_n$D   formula 2 wherein:
n is an integer ranging from 6 to 1000;
D is H or a C$_{1-8}$ alkyl group; and
each R is independently selected from H, halogen, a hydroxyl group, a halogenated C$_{1-8}$ alkyl group, $R_{11}$, —OR$_{11}$ or $R_{11}$OR$_{12}$, wherein $R_{11}$ and $R_{12}$ are each independently selected from a straight-chain or branched-chain C$_{1-8}$ alkyl group, a phenyl group, a C$_{1-8}$ alkyl substituted phenyl group, a C$_{1-8}$ alkoxy substituted phenyl group, or a halogenated phenyl group;
at least one of $R_1$, $R_2$, $R_3$, $R_4$, $R_5$, $R_6$, $R_7$, $R_8$, $R_9$, and $R_{10}$ is X, wherein not both $R_1$ and $R_6$ are X, and not both $R_5$ and $R_{10}$ are X;
Y is selected from a group having the following constitutional formula: —O—, —S—, —CH$_2$—, —CH(CH$_3$)$_2$—, —CH(CH$_3$)(CH$_2$CH$_3$)—, —CH(CH$_3$)(Ph)-, —CH(Ph)$_2$-, —CH(COOCH$_3$)—, —CH(COOCH$_2$CH$_2$CH$_2$CH$_3$)—, and —S(O)$_2$—; and
a mass ratio of the polyether polyol to the positive electrode active material ranges from 0.0005 to 0.040.

7. The positive electrode plate according to claim 6, wherein the positive electrode plate has a flexibility that:
allows the positive electrode plate to be crack-free under a pressure of a winding needle having a diameter less than or equal to 3.0 mm; or
causes the positive electrode plate to produce cracks under a pressure of a winding needle having a diameter equal to 3.0 mm, and allows the positive electrode plate to be crack-free under a pressure of a winding needle having a diameter equal to 4.0 mm.

8. The positive electrode plate according to claim 6, wherein:
an infiltration of the positive electrode plate in an electrolyte is 2% to 20% higher than an infiltration of a positive electrode plate without the polyether polyol in the electrolyte.

9. A secondary battery, comprising the positive electrode plate according to claim 6.

10. The positive electrode plate according to claim 6, wherein the positive electrode film layer comprises a first layer and a second layer, wherein the first layer is closer to the positive electrode current collector than the second layer, the first layer comprises the positive electrode active material and the polyether polyol, the second layer comprises the positive electrode active material and the polyether polyol, a mass percentage of the polyether polyol in the first layer is greater than 0 and smaller than or equal to 0.04, and a mass percentage of the polyether polyol in the second layer is in a range from 0.0005 to 0.004.

11. The positive electrode plate according to claim 10, wherein the the first layer and the second layer are parallel to the positive electrode current collector and superimposed with each other.

12. The positive electrode plate according to claim 6, wherein:
the positive electrode active material is selected from a group consisting of at least one of lithium iron phosphate, lithium manganese iron phosphate, lithium manganese oxide, lithium nickel cobalt manganese oxide, lithium nickel cobalt aluminate, lithium nickel oxide, the a mixture thereof.

* * * * *